United States Patent [19]

Sih

[11] 4,283,350

[45] Aug. 11, 1981

[54] 19,20-DIDEHYDRO-PG$_2$ AMIDES

[75] Inventor: John C. Sih, Kalamazoo, Mich.

[73] Assignee: The Upjohn Company, Kalamazoo, Mich.

[21] Appl. No.: 85,738

[22] Filed: Oct. 17, 1979

Related U.S. Application Data

[62] Division of Ser. No. 26,066, Apr. 2, 1979, Pat. No. 4,243,611.

[51] Int. Cl.$^3$ .................. C07C 177/00; C07C 103/19
[52] U.S. Cl. .................................. 564/189; 424/320; 424/324
[58] Field of Search ................................... 260/557 R

[56] References Cited

U.S. PATENT DOCUMENTS

| | | | |
|---|---|---|---|
| 3,919,285 | 11/1975 | Axen | 260/408 |
| 4,064,351 | 12/1977 | Sakai et al. | 560/121 |
| 4,098,805 | 7/1978 | Bundy | 260/559 R |
| 4,191,694 | 3/1980 | Skuballa et al. | 542/426 |

*Primary Examiner*—Arthur P. Demers
*Attorney, Agent, or Firm*—Robert A. Armitage

[57] ABSTRACT

The present invention provides novel 19,20-didehydro-PG$_2$ amides methods for their preparation and pharmacological use for the induction of prostaglandin-like effect.

1 Claim, No Drawings

19,20-DIDEHYDRO-PG₂ AMIDES

CROSS REFERENCE TO RELATED APPLICATIONS

The present application is a division of Ser. No. 026,066, filed Apr. 2, 1979 now pending issuance as a U.S. Pat. No. 4,243,611.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydro-PG compounds. Most particularly, the present invention relates to novel 19,20-didehydro-PG₂ amides, a disclosure of the preparation and use of which is incorporated here by reference from U.S. Pat. No. 4,228,104.

PRIOR ART

Prostaglandin analogs exhibiting unsaturation in the C-17, C-18, or C-20 position are known in the art. See, for example, U.S. Pat. No. 3,919,285 German Offenlegungsschrift 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

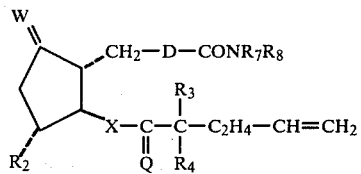

wherein D is
(1) cis—CH=CH—CH₂—(CH₂)$_g$—CH₂—,
(2) cis—CH=CH—CH₂—(CH₂)$_g$—CF₂—,
(3) cis—CH₂—CH=CH—CH₂—CH₂—,
(4) trans—(CH₂)₃—CH=CH—, wherein Q is

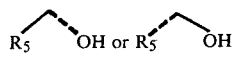

wherein R₅ is hydrogen or methyl, wherein R₇ and R₈ are
hydrogen, alkyl of one to 12 carbon atoms, inclusive, benzyl, or phenyl, being the same or different.
wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro; wherein W is

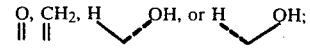

and wherein X is cis—or trans—CH=CH— or —C≡C—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

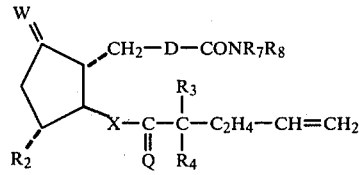

wherein D is
(1) cis—CH=CH—CH₂—(CH₂)$_g$—CH₂—,
(2) cis—CH=CH—CH₂—(CH₂)$_g$—CF₂—,
(3) cis—CH₂—CH=CH—CH₂—CH₂—,
(4) trans-(CH₂)₃—CH=CH—,
wherein Q is

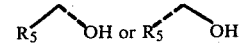

wherein R₅ is hydrogen or methyl, wherein R₇ and R₈ are
hydrogen, alkyl of one to 12 carbon atoms, inclusive, benzyl, or phenyl, being the same or different. wherein R₂ is hydrogen, hydroxyl, or hydroxymethyl; wherein R₃ and R₄ are hydrogen, methyl, or fluoro, being the same or different, with the proviso that one of R₃ and R₄ is fluoro only when the other is hydrogen or fluoro;
wherein W is

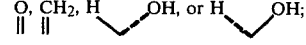

and wherein X is cis—or trans—CH=CH— or —C≡C—.

* * * * *

UNITED STATES PATENT OFFICE
CERTIFICATE OF CORRECTION

Patent No. 4,283,350　　　　Dated 11 August 1981

Inventor(s) John C. Sih

It is certified that error appears in the above-identified patent and that said Letters Patent are hereby corrected as shown below:

Column 1, line 46, and Column 2, line 33, "wherein Q is" should read -- wherein g is zero, one, 2, or 3; wherein Q is --

Signed and Sealed this

Third Day of November 1981

[SEAL]

Attest:

GERALD J. MOSSINGHOFF

Attesting Officer　　Commissioner of Patents and Trademarks